(12) United States Patent
Van Haute (10) Patent No.: US 9,091,024 B2
(45) Date of Patent: Jul. 28, 2015

(54) METHOD TO PRESERVE NATIVE STARCH PRESENT IN PULP IN A PAPERMAKING PROCESS

(71) Applicant: Buckman Laboratories International, Inc., Memphis, TN (US)

(72) Inventor: Eddie Van Haute, Ghent (BE)

(73) Assignee: Buckman Laboratories International, Inc., Memphis, TN (US)

(*) Notice: Subject to any disclaimer, the term of this patent is extended or adjusted under 35 U.S.C. 154(b) by 0 days.

(21) Appl. No.: 14/277,888

(22) Filed: May 15, 2014

(65) Prior Publication Data

US 2014/0246160 A1    Sep. 4, 2014

Related U.S. Application Data

(62) Division of application No. 13/909,119, filed on Jun. 4, 2013, now Pat. No. 8,764,942.

(60) Provisional application No. 61/655,678, filed on Jun. 5, 2012.

(51) Int. Cl.
*D21H 17/11* (2006.01)
*D21H 21/36* (2006.01)
(Continued)

(52) U.S. Cl.
CPC ...... *D21H 17/11* (2013.01); *C02F 3/28* (2013.01); *D06M 16/00* (2013.01); *D21C 3/18* (2013.01);
(Continued)

(58) Field of Classification Search
CPC ....... D21H 21/36; D21H 21/04; D21H 11/14; D21H 17/28; D21H 17/11; D21C 9/005; D21C 9/12; D21C 3/18; D21C 3/20; C02F 1/50; C02F 1/76; C02F 2101/10; C02F 2103/08; C02F 2303/22; C02F 3/28; C04B 18/24; D06M 16/00; Y10S 210/928
USPC ................. 162/70, 72, 87–90, 141, 147, 158, 162/160–161, 175, 183, 198; 210/749, 754, 210/764; 424/600, 661, 664, 641; 422/37
See application file for complete search history.

(56) References Cited

U.S. PATENT DOCUMENTS 1,940,592 A    12/1933   Henderson
2,061,031 A    11/1936   Henderson
(Continued)

FOREIGN PATENT DOCUMENTS

EP    0517102 A1    12/1992
WO    2013124542 A1    8/2013
(Continued)

OTHER PUBLICATIONS

International Search Report and Written Opinion issued in corresponding International Patent Application No. PCT/US2013/043962 dated Sep. 30, 2013 (16 pages).

*Primary Examiner* — Jose Fortuna
(74) *Attorney, Agent, or Firm* — Kilyk & Bowersox, P.L.L.C.

(57) ABSTRACT

Methods to preserve starch present in pulp are provided and also methods to control calcium precipitation and/or scaling in digesters or BOD systems. The methods can be performed as part of a papermaking process. Process water containing pulp can be treated with a chloramine. Process water containing pulp with native starch can receive a double treatment with at least one biocide, such as chloramine, and at least one oxidant, such as sodium hypochlorite. The treatment can be performed in any suitable manner. The treatment can be performed at one or more stages or locations in a papermaking system. A target residual chloramine value or range can be achieved by the treatment. Packaging sheets/boards and other paper products manufactured using the methods provided exhibit superior strength and other desirable characteristics.

15 Claims, 2 Drawing Sheets

(51) Int. Cl.
   *D21C 3/18* (2006.01)
   *C02F 1/76* (2006.01)
   *D21C 3/20* (2006.01)
   *D06M 16/00* (2006.01)
   *D21H 21/04* (2006.01)
   *C02F 3/28* (2006.01)
   *C02F 101/10* (2006.01)
   *C02F 103/28* (2006.01)

(52) U.S. Cl.
   CPC ............... *D21C 3/20* (2013.01); *D21H 21/04* (2013.01); *D21H 21/36* (2013.01); *C02F 1/76* (2013.01); *C02F 2101/10* (2013.01); *C02F 2103/28* (2013.01); *C02F 2303/22* (2013.01)

(56) References Cited

U.S. PATENT DOCUMENTS

| | | | |
|---|---|---|---|
| 3,328,294 A | | 6/1967 | Self et al. |
| 3,627,679 A | * | 12/1971 | Fuller ..................... 210/711 |
| 3,749,672 A | | 7/1973 | Golton et al. |
| 5,380,402 A | * | 1/1995 | Ryham et al. ............. 162/30.1 |
| 6,730,223 B1 | * | 5/2004 | Anderson et al. ........... 210/603 |
| 7,311,878 B2 | * | 12/2007 | Singleton et al. ............ 422/37 |
| 7,820,060 B2 | | 10/2010 | Mayer et al. |
| 8,168,072 B2 | * | 5/2012 | Barak ..................... 210/752 |
| 8,262,858 B2 | | 9/2012 | Duggirala et al. |
| 8,419,899 B2 | | 4/2013 | Xia et al. |
| 8,444,858 B2 | * | 5/2013 | Barak ..................... 210/696 |
| 8,764,942 B2 | * | 7/2014 | Van Haute ................. 162/198 |
| 2003/0121868 A1 | | 7/2003 | Barak |
| 2006/0231505 A1 | | 10/2006 | Mayer et al. |
| 2007/0045199 A1 | | 3/2007 | Mayer et al. |
| 2007/0049642 A1 | | 3/2007 | Singleton et al. |
| 2008/0017337 A1 | | 1/2008 | Duggirala et al. |
| 2011/0067832 A1 | | 3/2011 | Xia et al. |
| 2011/0159117 A1 | | 6/2011 | Mayer et al. |
| 2011/0174455 A1 | | 7/2011 | Duggirala et al. |
| 2012/0160779 A1 | | 6/2012 | Barak |
| 2013/0139980 A1 | * | 6/2013 | Ban et al. .................... 162/74 |
| 2013/0186583 A1 | | 7/2013 | Xia et al. |
| 2013/0319627 A1 | | 12/2013 | Van Haute |
| 2014/0246160 A1 | * | 9/2014 | Van Haute ................. 162/161 |

FOREIGN PATENT DOCUMENTS

| | | |
|---|---|---|
| WO | 2013184605 A1 | 12/2013 |
| WO | WO 2013184605 A1 * | 12/2013 |

* cited by examiner

FIG. 2

METHOD TO PRESERVE NATIVE STARCH PRESENT IN PULP IN A PAPERMAKING PROCESS

BACKGROUND OF THE INVENTION

This application is a divisional of U.S. patent application Ser. No. 13/909,119, filed Jun. 4, 2013, now U.S. Pat. No. 8,764,942, which in turn claims the benefit under 35 U.S.C. §119(e) of prior U.S. Provisional Patent Application No. 61/655,678, filed Jun. 5, 2012, which is incorporated in its entirety by reference herein.

The present invention relates to papermaking and/or the use of recycled paper/paperboard, and also relates to preserving the starch content of pulp during paper and packaging manufacturing, and further relates to controlling calcium precipitation and/or scaling in the treatment of waste water effluents.

Recycling is a major factor in the modern green economy and is particularly significant in the paper industry's goal to become more efficient and environmentally sustainable. Use of recycled pulp in paper and packaging manufacturing, however, presents several obstacles to achieving high-quality product. Recycled pulp, for example, derived from old corrugated cardboard, writing/printing grades sized or coated with starch, contain starch, usually at high levels, and are beneficial to making recycled paper/paperboard. The grades of paper/cardboard to be recycled also have beneficial levels of $CaCO_3$. Unfortunately, this starch content can become substantially degraded during manufacturing as can supplemental starch added during the manufacturing. Less starch in the resulting product means a loss of or lower mechanical properties in the paper/paperboard product made from the pulp. Further, the calcium found in pulp, such as pulp from recycled sources, can cause calcium precipitation, scaling or fouling in the post treatment of process water that occurs after pulp removal.

More specifically, in the past, numerous papermaking plants (especially those using recycled paper) have experienced numerous problems that may have been related to bacterial problems. However, when the standard approach to combating bacteria was attempted, no success was achieved. Biocides typically used in the papermaking industry and/or typical biocide treatments did not solve the following problems that were being seen in many machines making packaging papers. Those in the industry could not understand what was the exact problem and could not determine a solution to the problem. The present inventor however, determined that a particular microbial activity initiated the following sequence:

Microorganisms release amylases into the papermaking system.

These extracellular enzymes degrade starch into glucose oligomers (e.g., maltose) and glucose (the starch for instance, comes from waste paper, broke and/or wet end additive starch).

The oligomers and monomers are taken up by bacteria and are fermented producing volatile fatty acid (VFAs).

VFAs decrease the process pH (from 7 or higher to 6.5-6 or lower).

The fermentation process is accompanied by an increase in conductivity and decrease in redox potential.

The pH in localized areas around fermenting bacteria can be as low as 1 to 4.

Low pH dissolves calcium carbonate filler (for instance as present in waste paper) into soluble calcium $Ca^{2+}$ (and $CO_2$).

At this point, the problems only get worse: (1) increased growth of fermenting bacteria results in increased production of extracellular amylases; (2) any starch added for strength in the wet end (between mixing chest and head box) is degraded; (3) the glucose oligomers encourage even more growth of microorganisms and so increase slime and/or other bacteria problems; (4) VFAs are a cause of serious odor problems in the paper as well as in the production environment and/or in the surroundings, potentially including habitation areas; (5) when calcium carbonate is dissolved and stabilized by VFAs, filler (e.g., from waste paper) is lost, essentially a loss of raw material; and/or (6) dissolved calcium can cause deposit or scaling problems.

In mills utilizing anaerobic digesters for waste water treatment, another related problem can develop, as follows:

VFAs react to stabilize dissolved calcium (as VFA-Ca salts) and carry that calcium into the waste water treatment system.

With conversion of VFAs into $CH_4$ and $CO_2$ and a pH increase in the anaerobic digester, calcium scale forms; if excessive scale is formed this can shut down the waste treatment system, which in turn could cause the shutdown of the mill for cleaning of the anaerobic digester.

In mills utilizing aerobic digesters or ponds for waste water treatment, alone or in combination with anaerobic digesters, problems with $CaCO_3$ fall-out can develop, as follows:

VFAs react to stabilize dissolved calcium (as VFA-Ca salts) and carry that calcium into the waste water treatment system.

With (further) degradation of VFAs in the effluent and with further pH increase during the effluent treatment, calcium carbonate can precipitate resulting in scaling (aerobic reactors) or excessive sludge formation (in aerobic ponds). This can lead to increased downtime for maintenance and cleaning and can cause significant cost for the disposal of $CaCO_3$-rich sludge as chemical waste.

The present inventor was the first to understand the root of the problem and how to prevent and/or control this problem. The approach used by the present inventor, as described herein, is to reduce or prevent the breakdown of starch by microbiological activity in the paper mill. The root causes of the problem are in summary:

The bacteria and the amylase enzymes produced by the bacteria in the paper machines, because amylase enzymes are very efficient in breaking down starch, for instance, to maltose and glucose.

The stimulation of fermentation metabolism of facultative anaerobic bacteria by high glucose and sugar content in the process water resulting in high levels of VFAs being produced which are at the origin of the solubilisation of calcium filler in the process.

Thus, the present inventor determined that the best way to solve this problem was to get ahead of the problem and stop the terrible chain of events that are detailed above.

SUMMARY OF THE PRESENT INVENTION

It is therefore a feature of the present invention to improve strength in paper products (especially ones from recycled pulp or pulp from recycled sources) such as packaging sheets/boards, fluting, liner, test liner, single/multilayer and the like, by preserving the starch content of pulp used to manufacture the same. The treatment of the present invention can be used on Foudrinier and on roundformer machines.

Another feature of the present invention is to increase the efficiency of wet end additives in paper and packaging manufacturing. This for instance can be achieved through reduction of Ca$^{2+}$, pH increase, and/or lower conductivity.

A further feature of the present invention is to reduce odor-causing materials that can form during paper and packaging manufacturing.

Yet another feature of the present invention is the reduction of holes and microbiological-related breaks in paper and packaging being formed and in the completed product.

Another feature of the present invention is the preservation of pre-existing and/or newly added, strength-imparting (native) starch and/or preexisting and/or newly formed starch-cellulose complexes in recycled pulp and/or broke and/or other pulp source material from amylase degradation to allow efficient recovery and transfer of the pre-existing and/or newly added starch and/or preexisting and/or newly formed starch-cellulose complexes into a new sheet manufactured with the recycled pulp or broke.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a method to preserve starch present in pulp and in process waters. The method can be performed as part of a papermaking process. Process water containing pulp can be treated with a chloramine(s). The treatment can be performed in any suitable manner. The treatment can be continuous, substantially continuous, intermittent, cyclic, batch, or any combination thereof. Preferably the treatment maintains an effective amount of chloramine in the process water to achieve one or more benefits mentioned here and generally this effective amount is achieved by maintaining a residual amount of chloramine in the process water over a long continuous period of time. The treatment can be performed at one or more stages or locations in a papermaking system. For example, the treatment can be performed in a vessel such as a head box, and/or at one or more locations upstream and/or downstream of the headbox. A target residual chloramine value or range can be achieved by the treatment. For example, the process water can have a residual chloramine amount of from about 0.3 ppm to about 15 ppm (or chlorine equivalents). The ppm level is expressed as chlorine equivalents as is known and understood by those skilled in the art, and are not as actual chloramine ppm's in the process water. This residual amount can be determined, for instance, at the headbox, or just prior or just after the headbox (as just one example of a measurement location). The starch can be present in the pulp in a desired amount. For example, the starch can be present in the pulp in an amount of at least about 0.001 wt % based on the total weight of dried pulp fiber, such as 0.1 wt % or higher, or 1 wt % or higher, based on the total weight of dried pulp fiber. The present invention includes the surprising and unexpected discovery that chloramine when used in sufficient quantities and in a substantially continuous or continuous manner, can dramatically preserve starch content, such as, but not limited to cationic starch and/or native starch from size, coatings, sprays, and/or glues, that is present in the pulp, thus leading to packaging and paper products with enhanced properties including strength.

The present invention relates to a method for microorganism control and starch protection in pulp in a papermaking process or other process which comprises a dual treatment of process water containing pulp with biocide and oxidant. The biocide (e.g., chloramine and/or other biocides) can reduce or eliminate microorganisms capable of producing starch-degrading enzymes, such as amylase (such as α-amylase) or other starch-degrading enzymes, in the process water. The oxidant (e.g., sodium hypochlorite and/or other oxidants) can provide enzyme control to eliminate residual enzymatic activity of starch-degrading enzymes (such as those produced by microorganisms) or other enzymes. With the indicated dual treatment, enzyme substrates (such as native starches or other enzyme substrates) can be protected from degradation by such enzymes. The dual treatment method can reduce or eliminate counts of bacteria and/or other microorganisms that are starch-degrading enzyme producing and/or other microorganisms, in process water containing the pulp as compared to treatment of the process water containing the pulp without the biocide and oxidant. The dual treatment further can reduce or eliminate starch-degrading enzyme counts in the treated process water as compared to treatment of the process water containing the pulp without the biocide and oxidant.

The present invention relates to a method to preserve pre-existing and newly added (native) starch and pre-existing and newly formed (native) starch-cellulose complexes present in pulp in a papermaking process comprising treating process water containing pulp comprising complexes or aggregates of cellulose and native starch, wherein the treating comprises separately adding chloramine and oxidant (e.g., sodium hypochlorite) to the process water. The starch-degrading enzyme content (e.g., amylase content) in the treated process water is reduced compared to a similar treatment of the process water without the oxidant. The method can be used to preserve pre-existing as well as newly formed (native) starch and starch-cellulose complexes in recycled pulp, broke, or both used in a papermaking process which comprises the indicated double treatment strategy. An oxidant, e.g., sodium hypochlorite (NaOCl), is used to reduce or eliminate starch-degrading enzyme (e.g., amylase) from a process, such as a papermaking process, and chloramine is separately used from the oxidant in the process to reduce or eliminate microbiological infection and prevent or at least reduce starch-degrading enzyme (e.g., amylase) production in the process from starch-degrading enzyme producing microorganisms. (Native) starch and starch-cellulose complexes in recycled paper or broke are preserved which can contribute to strength in new sheets manufactured with the recycled pulp or broke. Starch-degrading enzyme producing microorganisms, such as amylase-producing bacteria, can produce enzymes that can degrade free starch if present in the process water, and also starch that is complexed with cellulose in aggregates that are introduced into a papermaking process from recycled papers or broke and the like and/or formed in-situ from new starch (native or cationic) added to the process which forms new bonds with fiber. The present invention includes the surprising and unexpected discovery that (native) starch present in recycled pulp or broke that is not mechanically removable (e.g., by processes such as repulping, mixing, refining and other paper processes) is vulnerable to release by starch-degrading action (e.g., amylolytic action), wherein the indicated double treatment strategy can reduce or prevent such starch-degrading action (e.g., amylolytic action) to allow efficient recovery and transfer of the pre-existing (native) starch and starch-cellulose complexes into a new sheet manufactured with the recycled pulp or broke. The indicated double treatment strategy alternatively or additionally can reduce and/or prevent such starch-degrading action on newly added starch (native or cationic), which can be present in the process as free starch and/or in complexed form wherein new bonds are created in-situ between this new starch and fiber in the process. The indicated double treatment strategy can protect, at least partially or fully, such newly added starch and/or newly formed starch-fiber complexes from amylolytic action.

The methods of the present invention also have the added benefits of controlling the growth of microorganisms, reducing the production of volatile fatty acids (VFAs), preventing conductivity increases, preventing decreases in redox potential, lowering calcium dissolution, increasing pH, and/or minimizing precipitation on and/or scaling of machinery—especially in anaerobic digesters. The methods of the present invention can increase the efficiency of cationic wet end additives, for example, retention polymers, starches, and/or dry strength resins. Improved strength allows for lower strength additive costs, reduction in basis weight, and use of product in higher strength grade markets.

The methods of the present invention can result in maintaining or increasing filler and/or ash content in the sheet product. For instance, solid calcium that would have been dissolved in conventional systems, is instead retained in the sheet as a raw material. Lower calcium ion concentrations (lower precipitated calcium levels) lead to increased uptake of starch into sheets including binding of starch to filler particles. Reduction in chemistry usage is also realized in multiple contexts including in the paper machine and subsequently in a biological waste water plant. Increased machine output due to reduction in size press starch solids and the option to transition from size press to wet end starch addition are also made possible. Also, with the present invention, a drying energy reduction can be achieved by the elimination of (1 or 2 sides of 2-sided) size press. Reduction in the amount of sludge to be landfilled and reduction in effluent plant polymer treatment are further made possible by the methods of the present invention.

It is to be understood that both the foregoing general description and the following detailed description are exemplary and explanatory only and are intended to provide a further explanation of the present invention, as claimed.

The accompanying drawings, which are incorporated in and constitute a part of this application, illustrate some of the features of the present invention and together with the description, serve to explain the principles of the present invention.

BRIEF DESCRIPTION OF THE DRAWINGS

The present invention may be more fully understood with reference to the accompanying figures. The figures are intended to illustrate exemplary features of the present invention without limiting the scope of the invention.

DETAILED DESCRIPTION OF THE PRESENT INVENTION

In accordance with the present invention, a method to preserve starch present in pulp is provided. The method can be performed as part of a papermaking process.

A key point in achieving effective control of the problems detailed above is using the correct biocidal treatment, and this involves using the correct biocide, the correct dosage, the correct application point(s), maintaining the correct residual biocidal levels, and to keep doing this over an extended period of time. It was determined that high levels of one or more chloramines must be maintained to control the problems detailed above. Essentially, the present inventor determined that a very aggressive and persistent treatment schedule is needed as detailed herein.

In more detail, the method to preserve starch present in pulp can be incorporated into a papermaking process. For instance, the papermaking process can have a head box or roundformer machines, and the like. This location(s) can be a treatment area, though this is optional. The method involves treating process water containing the pulp or process water used in the pulp preparation and paper production process with one or more chloramines comprising monochloramine, such that the process water has a residual chloramine amount, such as in the amount of from 0.3 ppm to 15 ppm (chlorine equivalent) (as for instance measured at the head box or other location where pulp is present). The starch can be present in the pulp in an amount of at least 0.001 wt % based on weight of dried pulp fiber. Further details, options, and examples are provided below.

Process water containing pulp can be treated with one or more chloramines, for example monochloramine (MCA), dichloramine (DCA), or a combination thereof. A majority (by weight) of the chloramine can be MCA (such as at least 50.1%, at least 60%, at least 70%, at least 80%, at least 90%, at least 95%, at least 99% or 100% by weight of the chloramine present). The treatment can be performed in any suitable manner. The treatment can be continuous, substantially continuous, intermittent, cyclic, batch, or any combination thereof. The treatment can be performed at one or more stages or locations in a papermaking system. For example, the treatment can be performed in a vessel such as a head box, treating pulper, pulper fill water or dump chest, or any combinations thereof. Generally, the treatment(s) occurs where the pulp is present with the process water and/or the process paper prior to being combined with pulp can be pre-treated with the chloramine as described herein.

Methods of the present invention can comprise a method for microorganism control and starch protection in pulp in a papermaking process comprising a dual treatment of process water containing pulp with biocide and oxidant. The microorganisms that are controlled can be bacteria, fungi, yeasts, archaebacteria, or other microorganisms that can produce starch-degrading enzymes, such as in process water in a papermaking process or other processes. The microorganisms that can be controlled with the treatment can be predominantly bacteria, essentially entirely, or entirely bacteria. Infection control can be provided through the biocide (e.g., chloramine and/or other biocides) to reduce or eliminate the presence of microorganisms in the process water that are capable of producing starch-degrading enzymes, such as amylase (e.g., α-amylase) or other enzymes, to reduce production of starch complex-degrading enzymes and the presence thereof in the process water. α-amylase (alpha amylase) is an endo-amylase that can quickly reduce molecular weight and also release starch from cellulose. β-amylase (beta-amylase) and γ-amylase (gamma-amylase) are terminal amylases which release di/mono sugars. Without being limited to the scope of this invention, though β-amylase (beta-amylase) and γ-amylase typically may not have a main role relating to starch stability in papermaking, they can play a role in making the sugars ultimately available to bacteria, whether producing amylases or not. For purposes of the present invention, all or some or one of the amylase types α-amylase and/or β-amylase and/or γ-amylase can be controlled and/or prevented as described herein. By controlling and/or preventing α-amylase alone or with any other amylase type, the benefits of the present invention can be achieved. When reference is made to "amylase" herein, it can include one or more or all of the amylase types and preferably includes at least α-amylase. The oxidant (e.g., sodium hypochlorite and/or other oxidants) can provide enzyme control to reduce or eliminate residual enzymatic activity of starch-degrading enzymes (such as those produced by microorganisms) or other enzymes. With the indicated dual treatment, enzyme substrates (such as native starches and/or other enzyme substrates) can be protected from degradation by such enzymes. The microorganism control, such as microbial infection control, provided by the method can reduce or eliminate counts of bacteria and/or other microorganisms that are starch-degrading enzyme producing and/or other types of microorganisms, in process water containing the pulp as compared to treatment of the process water containing the pulp without the biocide and oxidant. The control of microorganisms that can be starch-degrading enzyme producing by the method can be to below detectible levels or other values. The dual treatment further can reduce or eliminate starch-degrading enzyme counts in the treated process water as compared to treatment of the process water containing the pulp without the biocide and oxidant. The control of starch-degrading enzymes by the method can be to below detectible levels or other values.

Methods of the present invention can comprise the use of the chloramine and at least one other active in a coordinated manner in the same process. Chloramine and oxidant (e.g., sodium hypochlorite (NaOCl)) can be used in a coordinated manner in the same process. Using these actives of chloramine and oxidant (e.g., sodium hypochlorite), a method to preserve pre-existing (native) starch and starch-cellulose complexes in recycled pulp or broke from starch-degrading enzymatic action, such as amylase degradation, in a paper-making process or other process using such recycled pulp or broke materials is provided. Native starch can be present in recycled pulp or broke from size, coatings, sprays, and/or glues. Rather than assuming that during pulping of recycled paper or broke and subsequent steps in the paper production process that existing complexes or aggregates of cellulose and starch are completely disrupted, it is a finding of the present invention that actually a substantial quantity of starch remains in tight association with cellulose in such materials. In a study, after pulping in water (uninfected and free of amylase) and several washing steps with water, no more starch can be recovered from the fiber fraction. However, in this study, when amylase is added to the water, a very significant amount of starch and starch degradation products are then still released, indicating that some fraction of the starch is present in tight association with the fiber that cannot be removed by mere mechanical means (such as pulping, refining or washing), but which can be released by specific amylase action. This discovery provides an explanation of how starch protected from (enzymatic) amylase degradation can contribute to strength. By preventing presence of amylase and amylase degradation of starch, not only is non-complexed or free starch protected that can be present in the process (e.g., as released from pulped fibers, in recycled or broke), but pre-existing cellulose-starch complexes are also protected. The pre-existing cellulose-starch complexes can contain native starch that is not mechanically removed by processes such as repulping, mixing, refining and other paper processes, or at least not as easily or to the same extent as starch not contained in cellulose-starch complexes. Such cellulose-starch complexes can be very efficiently retained in the new sheet to ensure the incorporation of a (substantial) fraction of the recycled starch into the new sheet. The indicated double treatment strategy alternatively or additionally can reduce and/or prevent such starch-degrading action on newly added starch (native or cationic), such as newly added starch that is not removed through pulpers or refiners, which can be present in the process as free starch and/or in complexed form wherein new bonds are created in-situ between this new starch and fiber in the process. In this way, new starch-fiber complexes may be formed in-situ during the process. The indicated double treatment strategy can protect such newly added starch and/or newly formed starch-fiber complexes from amylolytic action.

The existence of the cellulose-starch complexes in starch/calcium stabilization in industrial applications, with appropriate amylase control by a method of the present invention, has been shown in experimental tests.

With the indicated dual treatment of a method of the present invention, starch that returns with recycled fiber (e.g., fiber from old paper/paperboard, mixed office waste, coated fine paper, broke, and the like) can be protected from enzymatic degradation. This protection can be provided to many types of starch in such papers, such as for native starches derived from starch spraying, glues, coatings, size, and other starch sources. These starches typically have no active way of binding to cellulose in the newly formed sheet, and they can benefit from the protection of pre-existing starch-cellulose aggregates by preventing dissociation of such aggregates by undesired amylase degradation. Furthermore, eliminating amylase activity by a dual treatment of a method of the present invention can protect high molecular weight starch molecules that can impart better strength than low molecular weight molecules. Cationic starches can remain attached to cellulose in the process of repulping and making a new sheet. These molecules can benefit from the elimination of amylase in the process as it can preserve their high molecular weight against degradation to smaller less strength imparting molecules. For recycled starch that is protected from degradation by a method of the present invention, and especially for the cellulose-starch complexes, the protection can be provided for at least one of a) the recycled starch protected from amylase degradation which retains a high average molecular weight, such as in the range of from about $10^6$ to about $10^8$, such as determined by size exclusion chromatography, 2) free high molecular weight starch, and/or 3) cellulose-high molecular weight starch aggregates. The weight of starch in cellulose-starch complexes protected from amylase degradation by a method of the present invention can be on average higher than in aggregates not protected from degradation by the method.

These cellulose-starch complexes (aggregates) can contain filler, and preventing degradation of starch can contribute to increasing filler retention and ash increase in the new sheet. There may be pre-existing starch-filler and/or starch-filler-cellulose complexes that remain intact after repulping. Keeping starch intact in these complexes can benefit strength and filler retention. In a similar way that starch-cellulose complexes can be carried into a new sheet to thereby transfer the native starch into the new sheet (something it would not normally do very efficiently by itself), filler complexes may be kept intact and transferred efficiently from recycled paper used as a pulp source to a new sheet. This may explain at least in part how significant increases in ash content in a new sheet can be obtained with a papermaking method of the present invention when calcium is prevented from solubilisation.

In more detail, the method to preserve pre-existing starch and cellulose-starch complexes in recycled pulp, broke, or both can comprise a double treatment strategy. Sodium hypochlorite (NaOCl) or other oxidant can be used to specifically reduce or eliminate amylase from a process, such as a papermaking process, and chloramine can be separately used, from the sodium hypochlorite or other oxidant, in the process to reduce or eliminate microbiological infection and prevent amylase production in the process. Chloramine reacts with the free chlorine of NaOCl or free halogen of other halogen-releasing oxidant, resulting in destruction of both actives. To prevent mixing of these actives in process water, separate addition positions for these actives in a process, sequential additions of these actives from the same position in a process, or both, can be used for the additions of chloramine and NaOCl to prevent them from mixing in the process. NaOCl can be added in sub-demand concentrations upstream of chloramine addition (or chloramine re-addition following an earlier chloramine addition and exhaustion thereof), wherein free chlorine will not move forward from its position of addition, or other strategies can be used to keep the chemicals apart in the process waters. Minor amounts of the NaOCl and chloramine below the detection limit for free chlorine or mca in process waters of 0.05-0.1 ppm as chlorine may be allowed to mix or inadvertently mix in the process solution (e.g. 5 wt % or less). The amount of chloramine added to the process solution can be an amount effective to reduce or eliminate microorganisms that can produce starch-degrading enzymes, and the amount of NaOCl added to the process solution can be an amount effective to provide amylase control to eliminate or at least reduce residual activity of the enzyme.

As an option, a "sacrificial" oxidant (examples are hydrogen peroxide ($H_2O_2$) or sodium hypochlorite (NaOCl)) can additionally be used to eliminate reducing agents other than microbiological from the process water. This sacrificial oxidant treatment can be used in combination with the chloramine treatment described herein. The sacrificial oxidant, if used in combination with the indicated method which provides the dual treatment including control of microbial infection and starch-degrading enzymes, can be used in addition to the same or different kind of oxidant used for the indicated dual treatment. The sacrificial oxidant, if used, can be added in the same production line as the chloramine, but not necessarily at the same time. As indicated, chloramine tends to react with the free chlorine of NaOCl or free halogen of other halogen-releasing oxidant, and preferably, these actives, when both are used in a process, are used separately.

As used herein, "preserve" or variants such as "preserves," "preservation," or "preserving," refers to a reduction and/or prevention in the decomposition of starch or a component thereof, such as amylose or amylopectin, in a composition that contains one or more starch decomposing enzyme and starch. The amount of reduction can be measured in relative terms by determining the starch level in a composition containing a starch decomposing enzyme, starch, and chloramine, in comparison to the same composition without the presence of chloramine, for a similar monitoring period. The starch levels can be assayed by conventional means used for that purpose. Other monitoring tools can be used, such as size exclusion chromatography which in addition to quantity also describes quality of the starch by giving information on molecular weight distribution in the starch and relative contribution of different molecular weights to the starch mix. The mechanism of the effect on the activity and/or production of enzymes is not particularly limited. The mechanism can at least partly reduce or prevent the effects of the enzymes to catalyze decomposition of starch, and does not require or exclude control of the microorganisms per se that produce the enzymes.

The pulp used in the present invention can be any suitable variety of pulp or combination of pulps. The pulp can be derived from hardwood, softwood, or a combination thereof. The pulp can be virgin, recycled, or a combination thereof. The pulp can be obtained from one or more sources such as broke, recycled packaging, old corrugated containers (OCC), mixed office waste (MOW), coated fine paper, baled mixed paper, sorted office paper, deinking grade newsprint, news blank, boxboard, boxboard with polymer, waxed boxboard, boxboard with foil, baled corrugated cardboard, waxed corrugated cardboard, beer carton waste, double lined kraft, bleached kraft, lightly printed bleached kraft, printed bleached kraft, colored kraft, brown kraft, kraft multiwall bag waste, kraft multiwall polybag waste, carrier stock, mixed envelope (new), white envelope, plastic windowed white envelope, colored envelope, plastic windowed colored envelope, kraft envelope, plastic windowed kraft envelope, printed kraft envelope, plastic windowed printed kraft envelope, white ledger, manifold white ledger, laser printed white ledger, colored ledger, manifold colored ledger, super ledger, carbon interleafed ledger, carbonless thermal ledger paper, hard white, mixed tab cards, manila tab cards, colored tab cards, manila file folder stock, soft white, ground wood fiber, magazines, magazines with hot melt, books, book stock, waxed cup stock, glassine, aseptic packaging, solid fiber containers, or any combination thereof. Starch can be present in recycled papers, such as broke, recycled packaging, old corrugated containers (OCC), mixed office waste (MOW), coated fine papers or other printing papers, or other indicated recycled papers, and in general all recycled cellulosic materials containing starch. The pulp can contain at least about 1.0 wt % post-consumer content, at least about 10 wt % post-consumer content, at least about 25 wt % post-consumer content, at least about 50 wt % post-consumer content, at least about 60 wt % post-consumer content, at least about 75 wt % post-consumer content, at least about 90 wt % post-consumer content, at least about 95 wt % post-consumer content, at least about 99 wt % post-consumer content, or 100 wt % post-consumer content based on the total weight of dried pulp.

The pulp source and/or pulp can contain any desired amount of starch. For example, the pulp source and/or pulp can contain starch in an amount of at least 0.1 kg/Tonne (1 Tonne, is a metric tonne=2200 lbs.), at least about 0.5 kg/tonne, at least about 1 kg/tonne, at least about 5 kg/tonne, at least about 10 kg/tonne, at least about 15 kg/tonne, at least about 20 kg/tonne, at least about 40 kg/tonne, at least about 45 kg/tonne, at least about 50 kg/tonne, at least about 75 kg/tonne, at least about 100 kg/tonne, at least about 250 kg/tonne, greater than about 500 kg/tonne, or a range including one or more of such amounts. The starch can be present in the pulp at a desired amount based on the total weight of dried pulp fiber. For example, the starch can be present in the pulp in an amount of at least about 0.001 wt %, at least about 0.01 wt %, at least about 0.05 wt %, at least about 0.10 wt %, at least about 0.50 wt %, at least about 1.0 wt %, at least about 5.0 wt %, at least about 10 wt %, at least about 15 wt %, at least about 25 wt %, at least about 50 wt % based on the total weight of dried pulp fiber, or a range including one or more of such amounts. For example, the starch content can be at least about 10 wt % including from about 2.0 wt % to about 3.0% wet end cationic starch, from about 2.0 wt % to about 5.0 wt % size double sided stock, and from about 1.0% to about 4.0% starch from glue based on the total weight of dried pulp fiber. The starch that is present in the pulp and/or process water can be a result of the starch present in the pulp (such as starch that is from recycled sources such as packaging and/or paperboard) and/or can be a result of additional starch added to the pulp and/or process water.

Starch can be measured, before, after, and/or during treatment of the pulp using any suitable or desired method. Starch molecular weight (MW) distribution can be measured, for example, through size exclusion chromatography. The methods of the present invention can enable an increased quantity and average molecular weight of starch recovered from recycled fiber as well as broke in the context of virgin fiber packaging mills. Increased MW of starch helps achieve improved mechanical properties. The average MW in Daltons of amylose, amylopectin, and/or total starch in the pulp can be at least $1.0 \times 10^3$ D, at least $1.0 \times 10^4$ D, at least $1.0 \times 10^5$ D, at least $5.0 \times 10^5$ D, at least $1.0 \times 10^6$ D, at least $2.5 \times 10^6$ D, at least $5.0 \times 10^6$ D, at least $7.5 \times 10^6$ D, or at least $1.0 \times 10^7$ D.

The starch can be endogenous and/or exogenous to the pulp source and/or pulp. The pulp can be supplemented with additional starch at any desired time point, location, or rate. The starch can be obtained from any source or combination of sources. Any kind of starch or combination of starches can be used. The starch can have any desirable amounts and/or relative amounts of amylose and amylopectin. For example, the starch can contain from about 5.0 wt % to about 50 wt % amylose and from about 50 wt % to about 95 wt % amylopectin, from about 10 wt % to about 35 wt % amylose and from about 65 wt % to about 90 wt % amylopectin, or from about 20 wt % to about 25 wt % amylose and from about 75 wt % to about 80 wt % amylopectin based on the total weight of the starch. The starch can contain cationic starch, anionic starch, or a combination thereof. The starch can be modified, unmodified, or a combination thereof. Modified starch can include, for example, one or more of hydroxyethyl starch, carboxymethylated starch, dextrin, acid-treated starch, alkaline-treated starch, bleached starch, oxidized starch, enzyme-treated starch, mono starch phosphate, distarch phosphate, phosphated distarch phosphate, acetylated distarch phosphate, starch acetate, acetylated distarch adipate, hydroxypropyl starch, hydroxypropyl distarch phosphate, hydroxypropyl distarch glycerol, starch sodium octenyl succinate, an acetylated oxidized starch, or any combinations thereof.

With the present invention, the process water containing the pulp has very low amylolytic bacteria counts and/or other bacteria. The amylolytic bacteria can be present at less than about 0.1 colony forming units (cfu) per gram of pulp dry weight (d.w.), less than about 10 cfu/g pulp d.w., less than about 1,000 cfu/g pulp d.w., less than about $1.0 \times 10^5$ cfu/g pulp d.w., less than about $1.0 \times 10^6$ cfu/g pulp d.w., less than about $1.0 \times 10^8$ cfu/g pulp d.w., less than about $1.0 \times 10^{10}$ cfu/g pulp d.w., less than about $1.0 \times 10^{12}$ cfu/g pulp d.w., less than about $1.0 \times 10^{15}$ cfu/g pulp d.w. Essentially, with the present invention, the amylolytic bacteria are controlled such that the bacteria cause no significant breakdown of the starch in the pulp. For instance, with the present invention, the amount of starch originally present (when added to the process water) is not reduced by more than 50% by weight once in the paper made from the pulp. Put another way, at least 50% by weight of the starting amount of starch in the starting pulp can make its way into the paper resulting from the pulp and this can be at least 60 wt %, at least 70 wt %, at least 80 wt %, at least 90 wt %, at least 95 wt %, such as from 60 wt % to 99 wt %.

The methods of the present invention can involve control or prevention of amylase production and/or activity (such as α-amylase production and/or activity). Control or prevention of amylase can be carried out using any suitable technique or combination of techniques. For example, amylase production can be controlled and/or prevented by killing microbes, or other microorganisms, that produce amylase or inhibiting production of amylase by microbes. External amylases, such as α-amylases, in recycled paper, broke, or other materials introduced into a papermaking process or other process, can be inactivated with use of the indicated double treatment that includes use of oxidant, such as NaOCl. Amylase (such as α-amylase) that is produced or otherwise present can be inhibited and/or degraded. By controlling or preventing, the retention of starch in the pulp and eventually into the resulting paper is achieved, for instance, in the amounts described in the above paragraph. The indicated double treatment strategy with chloramine and oxidant (e.g., NaOCl) can provide a paper sheet with greater strength as compared to a paper sheet made with a similar process that does not include the oxidant (e.g., NaOCl) treatment. In an alternative, when oxidant (e.g., NaOCl) addition is included in the process, less added strengthening aid may be needed to provide a similar level of product strength as compared to paper sheeting made with a similar process that excludes the oxidant (e.g., NaOCl) treatment.

Any suitable chloramine or combination of chloramine can be used in the methods of the present invention. The chloramine can contain monochloramine or other chloramine, or any combination thereof. The chloramine can be obtained from any suitable source. For example, BUSPERSE 2454 product, BUSAN 1215 product, and BUCKMAN 1250 product, available from Buckman Laboratories International, Inc., Memphis, Tenn., can be used as precursors (1:1 molar ratio to NaOCl in bleach) to form chloramine. The chloramine can be prepared accordingly to any suitable method. For example, chloramine can be produced by one or more technique described in U.S. Pat. Nos. 4,038,372, 4,789,539, 6,222,071, 7,045,659, and 7,070,751, which are incorporated herein in their entireties. The chloramine can be formed as a stock solution that can be introduced to the process water. The chloramine can be formed in-situ in the process water. The chloramine can be formed by reacting at least one ammonium salt with at least one chlorine-containing oxidant. The chloramine can be formed by reacting at least one ammonium salt with sodium hypochlorite or calcium hypochlorite or both. For example, the ammonium salt can be ammonium bromide, ammonium sulfate, ammonium hydroxide, ammonium chloride, or a combination thereof. Monochloramine can be produced by reacting 1 to 1 molar ratio of the ammonium salt and chlorine.

Any suitable oxidant or combination of oxidants can be used in the indicated dual treatment methods of the present invention as the oxidant used to reduce or eliminate starch-degrading enzymes, such as amylase. Oxidants can be used in the dual treatment method that are incompatible or compatible with monochloramine. As indicated, NaOCl is incompatible with monochloramine, wherein NaOCl releases free chlorine that reacts with the monochloramine and thus eliminates it. Other oxidants which are incompatible with chloramine which can be used are hypohalite compounds (e.g., $OBr^-$), halogen oxidants added through halogen stabilisers such as halogenated hydantoins (e.g., bromochloro-5,5-dimethylhydantoin or BCDMH), DMH with bleach, urea with bleach, and the like. For example, though NaOCl is illustrated herein, other alkali metal hypohalites or alkaline earth metal hypohalites can be used, including any combinations thereof. Hypohalite salts may be added to process water in liquid or solid particulate forms, depending on the specific material. Oxidants which are effective to reduce or eliminate starch-degrading enzymes that are compatible with monochloramine can be used. Compatible oxidants do not release free halogen that reacts with the monochloramine. The oxidants which can be compatible with monochloramine can be chlorine dioxide ($ClO_2$), peroxides such as hydrogen peroxide ($H_2O_2$), peracetic acid (PAA), perfluoric acid (PFA), or others, and in any combinations thereof.

Figure 1:
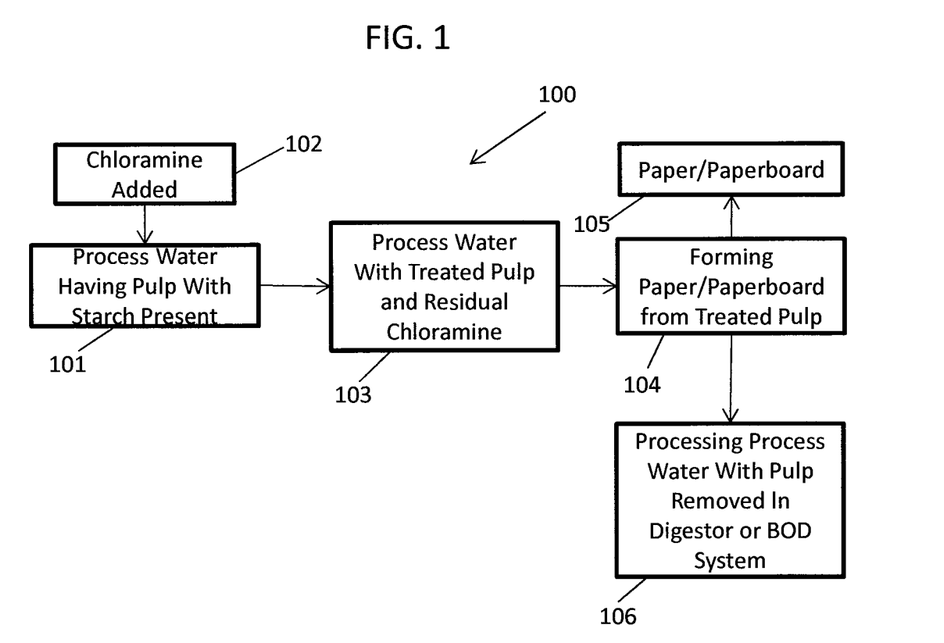
FIG. 1 is a process flow chart illustrating a method according to an example of the present application.

FIG. 1 shows a method, indicated as process 100 comprising steps 101-106, for the treatment of process water that contains pulp with chloramine. The treatment can be performed at one or more stages or locations in a papermaking system. For example, the treatment can be performed in a vessel such as a head box. The treating can occur at a head box, upstream of a head box, downstream of a head box, or any combination thereof. Multiple addition points per location can be interchangeable. In a system with a single water loop shared between pulper to machine, examples of addition points can include one or more of the following: pulper(s), pulper fill water, a dump chest, a mixing or machine chest, a head box, and/or white water. In a system with two water loops defining a stock preparation part and a machine part, examples of addition points can include one or more of the following: stock preparation, pulper(s), pulper fill water, a dump chest, stock chest(s), stock loop process water, a paper machine, a mixing or machine chest, a head box, broke, and white water. Stored broke can receive adequate treatment. If multiple lines (short/long) are employed, treatment can be maintained in at least one line, in more than one line, or in all lines.

The amount of chloramine and/or precursors used for treating the pulp can be constant or variable. A target residual chloramine value or range can be achieved by the treatment. For example, the process water can have a residual chloramine amount of from about 0.1 ppm to about 30 ppm, from about 0.3 ppm to about 15 ppm, from about 0.5 ppm to about 12 ppm, from about 1.0 ppm to about 10 ppm, from about 2.0 ppm to about 8.0 ppm, from about 4.0 to about 7.5 ppm, from about 5.0 to about 7.0 ppm in the process water containing the pulp. As stated, this amount can be considered a chlorine equivalent. This would also be applicable for white waters, and/or various filtrates—superclear, clear and cloudy. This residual chloramine amount can be an average chloramine amount based on a 24-hour period. The level of chloramine to pulp can be at least about 0.10 lb. chloramine per ton of dry pulp (1 ton=2000 lbs.), at least about 0.30 lb. of chloramine per ton of dry pulp, at least about 0.75 lb. of chloramine per ton of dry pulp, at least about 1.0 lb. of chloramine per ton of dry pulp, at least about 1.25 lbs. of chloramine per ton of dry pulp, at least about 1.6 lbs. of chloramine per ton of dry pulp, at least about 2.0 lbs. of chloramine per ton of dry pulp, at least about 2.5 lbs. of chloramine per ton of dry pulp, at least about 3.0 lbs. of chloramine per ton of dry pulp, or at least about 5.0 lbs. of chloramine per ton of dry pulp. The level of chloramine to pulp can be at least about 50 g of chloramine per tonne (1 tonne=2200 lbs.) of dry pulp, at least about 150 g of chloramine per tonne of dry pulp, at least about 350 g of chloramine per tonne of dry pulp, at least about 500 g of chloramine per tonne of dry pulp, at least about 700 g of chloramine per tonne of dry pulp, at least about 800 g of chloramine per tonne of dry pulp, at least about 1.0 kg of chloramine per tonne of dry pulp, at least about 1.25 kg of chloramine per tonne of dry pulp, at least about 1.5 kg of chloramine per tonne of dry pulp, at least about 3.0 kg of chloramine per tonne of dry pulp, or at least about 5.0 kg of chloramine per tonne of dry pulp.

The treatment of the pulp with chloramine can be continuous, substantially continuous, intermittent, cyclic, batch, or any combination thereof. Treatment can be repeated any desired number of times and treatments can be separated by constant or variable time periods. The addition of chloramine and/or precursors to the pulp can be continuous, substantially continuous, intermittent, cyclic, batch, or any combination thereof. The rate of addition of chloramine and/or precursors can be constant or variable. Chloramine, and/or precursors thereof, can be added in any manner to the process water, for example, by pouring, by nozzle, by spraying, by misting, by curtain, by weir, by fountain, by percolation, by mixing, by injection, or by any combination thereof. The process water can be treated for any period of time. For instance, on a substantially continuous or continuous basis, such as at least about 6.0 hours, at least about 12 hours, at least about 24 hours, at least about 36 hours, or at least about at least 7 days, at least 2 weeks, at least 1 month, at least 2 months, at least 3 months, from 1 day to 6 months, from 1 day to 12 months or more. The amount of chloramine added can be varied based on any one or combination of different factors, for example, starch concentration, amylase concentration, microbial concentration, conductivity, redox potential, turbidity, amount of pulp, cation concentration, anion concentration, calcium ion concentration, volatile fatty acid (VFA) concentration, and pH.

The process water can have a constant or variable pH during the treatment of the pulp with chloramine. The pH can be at least about 5.0, at least about 6.0, at least about 6.5, at least about 7.0, at least about 8.0, at least about 10.0, or at least about 12.0. The process water can have a constant or variable temperature during the treatment of the pulp with chloramine. For example, the temperature can be at least about 5° C., at least about 10° C., at least about 20° C., at least about 25° C., at least about 30° C., at least about 40° C., at least about 50° C., at least about 60° C., or at least about 75° C.

In the present invention, the minimizing of calcium ion formation in the process water is achieved. This prevents fouling of one or more components of the papermaking process and/or tanks/reactors. More importantly, by minimizing the calcium ion formation, this means that the calcium (e.g., calcium carbonate) stays with the pulp and eventually is present in the resulting paper product, and further this means that the calcium ion concentration in the process water (after pulp removal) is low thus resulting in controlled (or prevention of) calcium precipitation and/or scaling in the waste water treatment part of the process (such as the digesters and/or BOD systems). "Precipitation" can refer to settling or fall out of solids or insolubility, and "scaling" can refer to a specific process that forms deposits. For example, $Ca^{2+}$ ion levels in the process water can be less than about 5000 ppm, less than about 2500 ppm, less than about 1200 ppm, less than about 1000 ppm, less than about 800 ppm, less than about 500 ppm, less than about 250 ppm, or less than about 100 ppm, such as from 10 ppm to 5000 ppm, from 50 ppm to 3,000 ppm, from 100 ppm to 2,000 ppm. This is especially the case once the pulp is substantially or entirely removed from the process water and this calcium concentration would be right before entering the waste water treatment part, such as right before entering the digester (s) or other BOD treatment equipment.

The methods of the present invention can further include forming packaging sheets/boards. Such packaging sheets/boards can have any desirable starch content. For example, packaging sheets/boards can have a starch content of at least about 1.0 kg/ton (1 ton=2000 lbs.), at least about 2.5 kg/ton, at least about 5.0 kg/ton, or at least about 10.0 kg/ton of packaging sheets/boards. Strength of packaging sheets/boards and other paper products made using the methods of the present invention can be measured using any suitable technique, for example, the span compression test (SCT), the burst test, and/or the ring crush/Concora test. The present invention also provides systems employing the methods described herein as well as packaging and other paper products produced by the methods described herein. The methods described herein can be performed in aerobic systems, anaerobic systems, or any combination thereof.

As indicated above, the present invention can relate to a method to use chloramine and sodium hypochlorite in a coordinated manner in the same process. Chloramine (e.g., monochloramine) can provide excellent performance for cost in high demand systems as a biocide enabling the rigorous level of infection control that is required to keep amylase levels very low. In direct tests, chloramine as an oxidizing agent shows virtually no activity to inactivate amylases specifically, although it can be active with respect to other enzymes. NaOCl is an inefficient biocide in high demand systems, even at very high treatment rate. In direct tests, NaOCl is very efficient at inactivating amylases (and enzymes in general).

To provide these coordinated effects, chloramines can be added in the indicated dosages herein, and the oxidant (such as NaOCl) used to control starch-degrading enzymes can be added in dosages at from about 10 wt % to about 50 wt %, or from about 10 wt % to about 45 wt %, or from about 15 wt % to about 50 wt %, or from about 20 wt % to about 40 wt %, of the actual chlorine demand in the treated solution. The "chlorine demand" can be the total amount of chlorine which would be used up in reactions with all chlorine-reactable compounds in the process solution and without leaving residual chlorine therein. The indicated dosages herein for the chloramine and oxidant (e.g., NaOCl) can be the amount of the respective active added to the process solution that is not reacted with the other indicated double treatment active in the process solution, and thus available to treat the process solution. The oxidant sodium hypochlorite (NaOCl) can be added in an aqueous form. NaOCl can be used in the methods herein in dilute aqueous forms, such as aqueous forms which can contain up to about 15 wt % chlorine (e.g., from about 1 wt % to about 15 wt % NaOCl), or other concentrations.

As shown by experimental results in an example herein, it has been demonstrated in laboratory tests that the addition of NaOCl at from 10% to 50% of the actual chlorine demand in high demand solutions containing amylases was enough to reduce or eliminate the amylase activity. As indicated, a double treatment strategy can be provided wherein NaOCl is used to eliminate amylase from the process, and chloramine is used to eliminate infection and prevent amylase production in the process. The combination of both treatments in a process results in a much more efficient treatment wherein a synergy between both treatments is obtained. Chloramine reduces and keeps infection and amylases low, and NaOCl eliminates whatever amylases still exist, such as α-amylases, thereby prevents starch degradation and reduces nutrient availability for the infection. Amylases can come in with poor quality old papers (wet, infected, moulded). Chloramine does not usually have any impact on the incoming amylases. NaOCl also inactivates external amylases that come into the process. Other sources of external amylases could be process waters imported from untreated paper machines, reused (partially) treated effluents that replace fresh water. Another source of amylases can be recycled fiber stock chests, deinking fiber stock chests or broke chests that have (occasional) very long residence time which renders any infection control, also with monochloramine, problematic; NaOCl can be used to eliminate amylase from the stock used from such chests and such prevent further contamination of process waters with amylases.

Figure 2:
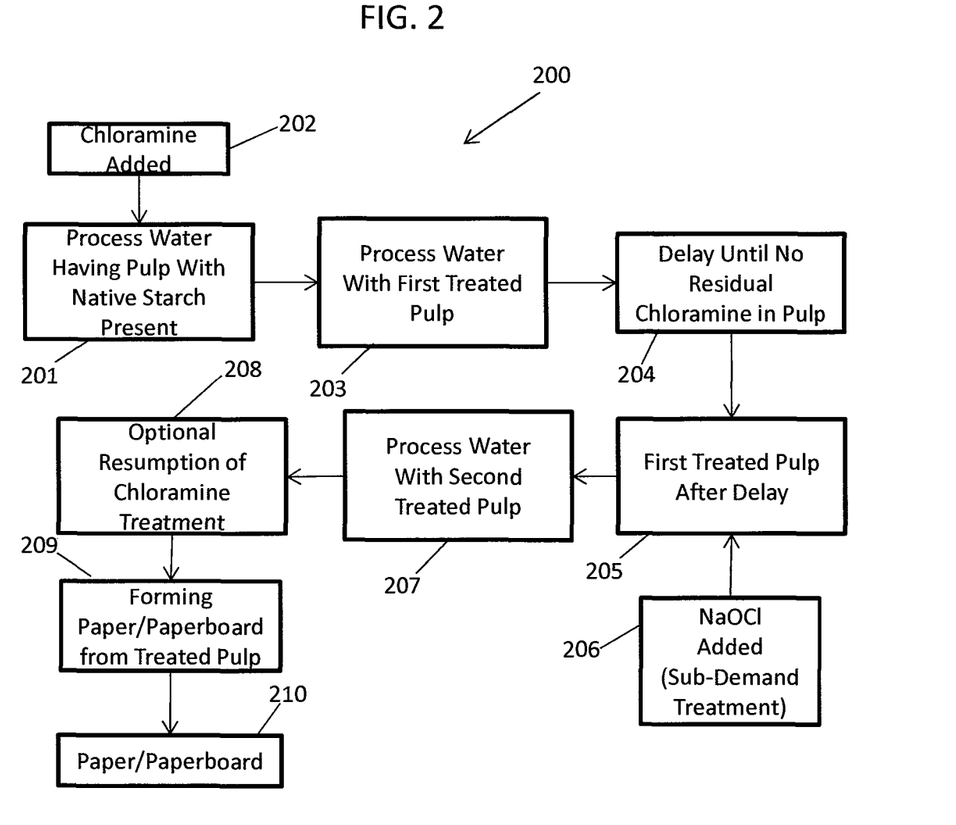
FIG. 2 is a process flow chart illustrating a method according to an example of the present application.

FIG. 2 shows a method, indicated as process 200 comprising steps 201-210, for the indicated double treatment of process water that contains pulp with native starch with chloramine and sodium hypochlorite. As indicated, in a method of treating process water with chloramine and an incompatible oxidant such as NaOCl or other free halogen-releasing oxidant, chloramine and free chlorine from NaOCl, and/or other incompatible oxidant, preferably are not present together in the process water because the chloramine reacts with the free chlorine resulting in destruction of the two actives. Therefore, both actives preferably are kept separated (or substantially separated) from each other in the process water undergoing processing. This separation of chloramine and NaOCl (or other incompatible oxidant), where used as the oxidant, in the process water can be achieved in different ways. NaOCl (or other incompatible oxidant) and chloramine can be added at different positions in the process and as both actives are consumed as they move further through the process this will prevent them from mixing. NaOCl (or other incompatible oxidant) and chloramine can be sequentially added from the same position with a time delay between their respective additions. If chloramine is added to the process water before NaOCl (or other incompatible oxidant) addition, the delay of the addition of the NaOCl (or other incompatible oxidant) can be controlled to allow for the level of previously added chloramine to be below about 5 ppm, or below 1 ppm, or below detectible limits. By properly Controlling chloramine addition upstream from the positions where NaOCl (or other incompatible oxidant) is added, the presence of chloramine at these positions can be prevented. In recycled fibre systems, typically residuals of chloramine are very low. After the chloramine treatment is stopped, if a chloramine residual is present it quickly disappears. After an appropriate (adjustable) delay after chloramine addition is stopped, NaOCl (or other incompatible oxidant) can be dosed. As indicated, NaOCl (or other incompatible oxidant) can be added in sub-demand concentrations, wherein free chlorine does not move forward from its position of addition before chloramine is added (or re-added). Places for adding the NaOCl (or other incompatible oxidant) in a papermaking process can be the pulper and high density chests, or other locations. After the NaOCl (or other incompatible oxidant) dosing is stopped, because a sub-demand treatment can be applied and no residual is present, chloramine dosing can resume, such as resume immediately. The resumed addition of chloramine after NaOCl (or other incompatible oxidant) addition can be optional, such as depending on the needs of the process system being treated. Both spatial and temporal separation of chloramine and NaOCl have been successfully used in tests done on industrial systems, whereby no mutual negative impact of the actives was detected. Experimental industrial results have shown that better efficacy of overall treatment can be obtained with lower chloramine addition rates, a lower overall cost of treatment, better strength characteristics of the new sheet, or combinations of these can be obtained. Experimental industrial results show that the method provides not only the efficient biocide/chloramine treatment, but it adds a specific double treatment approach with NaOCl that specifically targets the amylase in the process.

As indicated above, the present invention also relates to a method to control or prevent calcium precipitation and/or scaling in an aerobic or anaerobic digester(s) that processes process water used in papermaking and that contained calcium from pulp being process, the method comprising in a papermaking process, continuously treating process water containing said pulp with chloramine comprising monochloramine such that said process water, when said pulp is present, has a residual chloramine amount, such as from 0.3 ppm to 15 ppm (or the other residual amounts mentioned earlier), wherein calcium is present in said pulp, and then forming paper/paperboard from said pulp, and processing said process water, after pulp removal, to one or more digesters.

The present invention also relates to a method to control or prevent calcium precipitation and/or scaling in a biological oxygen demand reduction (BOD) system that processes process water used in papermaking and that contained calcium from pulp being processed, said method comprising in a papermaking process, continuously treating process water containing said pulp with chloramine comprising monochloramine such that said process water, when said pulp is present, has a residual chloramine amount of from 0.3 ppm to 15 ppm (or the other residual amounts mentioned earlier), wherein calcium is present in said pulp, and then forming paper/paperboard from said pulp, and processing said process water, after pulp removal, to said BOD system to reduce BODs.

In the methods above, involving the digesters and/or BOD systems, the calcium ion amount present in the process water after pulp removal can be 5000 ppm or less, 2000 ppm or less, 1000 ppm or less, 500 ppm or less, or from about 10 ppm to 500 ppm (based on the process water that reaches the digester or BOD system equipment).

In addition or in the alternative, the chemical oxygen demand (COD) can be measured and controlled by the present invention. The COD is a faster test method to determine or predict what the BOD is for the system. BOD testing can take days whereas COD testing can be minutes to hours to determine. One COD test procedure that can be used is the test described in *Standard Methods—For the Examination of Water and Wastewater,* $17^{th}$ Ed., Am. Public Health Assoc. et al, pp. 5-12, where the Chemical Oxygen Demand (5220B)/ Open Reflux Method. Thus with the present invention, COD demand can be controlled or reduced using the methods of the present invention. Essentially the nutrients that bacteria can feed on, like starch or the breakdown of starch can be reduced using the methods of the present invention, since the starch is retained in the pulp and eventually in the paper using the processes of the present invention.

The residual chloramine concentration of the process water, when entering the digester or BOD system equipment can be much lower, such as below 0.3 ppm (e.g., 0.00001 ppm or less, 0 ppm, 0.01 ppm or less, 0.1 ppm or less, 0.001 ppm or less) and the like.

With the present invention, the starting starch levels found in the pulp with process water (at the start of the papermaking process) compared to the starch levels in the pulp and process water (right before the separation of the pulp from the process water—e.g., right before the pulp is placed on the screen) is within 50% by weight, within 40% by weight, within 30% by weight, within 20% by weight, within 10% by weight, within 5% by weight, or within 1% by weight. In other words, with the present invention, the starch levels are preserved through the process and are not degraded or broken down by bacteria.

With the present invention, the difference between the ppm levels of the starting calcium levels (e.g. dissolved calcium, $Ca^{2+}$) found in the pulp with process water (at the start of the papermaking process) compared to the calcium levels of the process water after the pulp is removed is at most an increase of 500 ppm (+500 ppm or less), such as at most an increase of 250 ppm (+250 ppm or less), at most an increase of 100 ppm (+100 ppm or less), at most an increase of 50 ppm (+50 ppm or less), and more preferably, a decrease in the calcium levels, such as a decrease of at least 50 ppm (−50 ppm or more), a decrease of at least 100 ppm (−100 ppm or more), a decrease of at least 250 ppm (−250 ppm or more), a decrease of at least 500 ppm (−500 ppm or more), a decrease of at least 1000 ppm (−1000 ppm or more), a decrease of at least 2000 ppm (−2000 ppm or more), a decrease of at least 3000 ppm (−3000 ppm or more), with respect to starting versus final calcium levels in the process water as described above.

The following examples are given to illustrate the nature of the invention. It should be understood, however, that the present invention is not to be limited to the specific conditions or details set forth in these examples. Unless stated otherwise, in the Examples, the reference to "tonne" is a metric tonne and is based on "per tonne" of dry pulp.

EXAMPLES

Example 1

This example demonstrates one or more of the superior benefits of the present invention. A new anaerobic digester was being used at an effluent plant that received waste water from papermaking (after pulp removal). Prior to the present invention, the plant reported loss of performance of the anaerobic digester from calcium precipitation and/or scaling and also reported blocking of the digester from precipitation and/or scaling. The plant had to shut down the digester to clean the digester (scale removal) This resulted in significant down time for the plant and unscheduled expenses to clean the digester. The plant operators did not understand the cause of the problem or a solution. The present inventor offered an experimental trial to see if the present invention would work in the field. The process water that became the waste water that entered the digester was treated. In particular, the process water (which contained pulp) was treated with chloroamines (primarily monochloramine) in an amount of 300 g/tonne at the pulpers of the papermill and also at the top ply whitewater (WW) silo. This was done on a continuous basis. The amount of calcium ion concentration (dissolved in water) in the process water at the start of the pulp process (before the headbox) was measured and also the amount of calcium concentration right before entering the digester was measured and the difference in calcium was determined. Prior to using the present invention, the calcium ion concentration increased 2000 ppm. This was a very negative, undesired occurrence. Once the present invention's method was used for 2 to 3 days (continuously), the difference in calcium concentration was determined again, and the change in calcium concentration had eventually gone to a minus 2,500 ppm. In other words, the amount of dissolved calcium at the digester was lowered by over 2,500 ppm compared to the amount of calcium at the start of the pulping at the papermill. This was an incredible turn around, which prevented the fouling of the digesters. Also, due to reducing the calcium content, the resulting sludge can be considered anaerobic sludge and not chemical disposal.

Further, in the pulp mill where the process water (waste water) came from, the pulp was recycled pulp (including recycled packaging) and had a high starch content. Prior to the use of the present invention, as described above, the initial starch content at the time of mixing with water went down significantly during the processing of the pulp, such that the wet sheets formed from the pulp had a significantly reduced starch content. It was discovered, by the present inventor, that the starch was being broke down by amylolytic bacteria. By using the methods of the present invention, besides achieving control of the calcium precipitation and/or scaling, the present invention also controlled the consumption of starch by controlling the bacteria. As a result, significant levels of the starting amount of starch were preserved and incorporated into the paper formed from the pulp.

Example 2

This example also demonstrates one or more of the superior benefits of the present invention. An anaerobic digester was being used at different effluent plant that received waste water from papermaking (after pulp removal). Prior to the present invention, the plant reported loss of performance of the anaerobic digester from calcium precipitation and/or scaling and also reported blocking of the digester from precipitation and/or scaling. The plant had to shut down the digester to clean the digester (scale removal). This resulted in significant down time for the plant and unscheduled expenses to clean the digester. The plant operators did not understand the cause of the problem or a solution. The present inventor offered an experimental trial to see if the present invention would work in the field. The process water that became the waste water that entered the digester was treated. In particular, the process water (which contained pulp) was treated with chloroamines (primarily monochloramine) in an amount of 300 g/tonne to 600 g/tonne at the pulper dilution water of the papermill and also at the thick stock-before fractionation in an amount of 400 to 800 g/tonne, and at the whitewater (WW) flume in an amount of 400 to 800 g/tonne. This was done on a continuous basis. The amount of calcium ion concentration (dissolved in water) in the process water at the start of the pulp process (before the headbox) was measured and also the amount of calcium concentration right before entering the digester was measured and the difference in calcium was determined. Prior to using the present invention, the calcium ion concentration increased 4000 ppm. This was a very negative, undesired occurrence. Once the present invention's method was used for 2 to 3 days (continuously), the difference in calcium concentration was determined again, and the change in calcium concentration had eventually gone to a minus 700 ppm. In other words, the amount of calcium at the digester was lowered by over 500 ppm compared to the amount of calcium at the start of the pulping at the papermill. This was an incredible turn around, which prevented the fouling of the digesters. Also, due to reducing the calcium content, the resulting sludge can be considered anaerobic sludge and not chemical disposal.

Example 3

Experimental tests were conducted to evaluate the effects of adding NaOCl to high demand solutions containing amylases, including α-amylases.

In the experiments described below, amylase activity was measured using a synthetic α-amylase substrate, "RED-STARCH" obtained from MEGAZYME® (Ireland), and a test procedure developed that allows the use of this substrate in complex paper mill process waters including samples containing cellulose.

The indicated test procedure developed for testing paper mill samples for α-amylase activity includes preparation of the substrate by adding 1 g of powdered RED-STARCH substrate to 50 mL of 0.5 M KCl solution (7.45 g/100 ml), and warming up to 60° C. whilst shaking vigorously until dissolved. The prepared substrate can be used fresh or stored under refrigeration until used. A concentrated assay buffer solution was prepared as a 300 mM $CaCl_2.2H_2O$ solution (39.2 g/l), which for use, is diluted 200 times in the assay. Assays can be performed on any liquid sample recovered in a paper mill. Samples with high turbidity may interfere with the final measurement step. Accordingly, samples containing fiber can be filtered through a paper filter, and liquid from high consistency samples can be recovered by squeezing liquid from the sample. To perform the assay on a sample, 30 μl assay buffer, 3 ml RED-STARCH substrate solution, and a 3 ml test sample solution can be added to a 35 ml test vial, and mix and incubate the vial and contents at constant temperature (35-40° C.) for 30 minutes. The reaction is ended by adding 10 ml ethanol (denatured) or methanol and shaking vigorously, and then allowing the vial and its contents to stand for 2 minutes before filtering the contents through a paper filter. High molecular weight material can be removed by the filtering. Using a 10 ml syringe, the filtered liquid is passed through a 0.22 or 0.45 μm disposable filter cartridge. The liquid that passes through the cartridge is introduced into a spectrophotometer cuvette, and the absorbance (OD) of the reaction solution, and a separate reaction blank, are measured using a spectrophotometer. The reaction blank is prepared by adding 10 ml ethanol or methanol to a test vial first, then add 30 μl assay buffer, 3 ml red starch substrate solution, and a 3 ml test solution, and prepare the samples for measurement as above. The spectrophotometer can be a Hach DR/890 Colorimeter (Hach Company, Loveland Colo.), or other spectrophotometer device. Absorbance can be measured as optical density (OD). On incubation of the RED-STARCH substrate with α-amylase, the substrate can be depolymerized to produce low molecular weight dyed fragments which remain in solution on addition of alcohol to the reaction mixture. The measured value of OD is directly proportional to the α-amylase activity in the test sample. Most spectrophotometers have a scale that reads in OD (absorbance) units, which is a logarithmic scale. A user edited program can be entered into the DR/890 device, including choosing a wavelength of 510 mm at which absorbance is measured, using water as a blank (OD=0), and preparing a maximum α-amylase activity sample by adding a small amount of BUZYME® 2508 (Buckman Laboratories, Belgium) to water and using this in the assay (max. OD that can be measured is approximately 25). The range that is obtained with this program is very large and can suffice for all paper mill samples. Using this testing procedure, paper mill samples typically have absorbance values in the range of 1-7. If a sample gives a maximum reading, it can be diluted in water to determine a more precise value. Results can be represented as the actual number or as a percentage of the maximum reading of the procedure which is 25. The results in Table 1 below show results for α-amylase activity as a percentage of the maximum reading.

In the tests conducted, process water was used that was taken from a coated paper machine pulper fill water tank that was not being treated with an oxidizing program. First, the actual chlorine and monochloramine ($NH_2Cl$) demands of this process water were determined (Table 1). To this process water, a commercial α-amylase was added (BUZYME® 2508, at a 1/1000 mixture ratio. From this mix, 30 ml samples were prepared to which were added sub-demand quantities of NaOCl and monochloramine as shown in Table 1 below. These samples were allowed to incubate for 15 minutes at 40° C. before the α-amylase substrate RED-STARCH and the reaction buffer were added. After a contact time of 30 minutes at 40° C., the reaction was stopped by adding alcohol (denatured ethanol or methanol) and the remaining relative α-amylase activity in each sample determined as described in the method above (Table 1).

TABLE 1

| Oxidant demand (ppm Chlorine equivalent added) | | | |
|---|---|---|---|
| NaOCl 58 | | $NH_2Cl$ 13 | |
| NaOCl (as % of demand) | α-amylase activity | $NH_2Cl$ (as % of demand) | α-amylase activity |
| 0.0% | 100.0% | 0.0% | 100.0% |
| 10.0% | 99.2% | 10.0% | 100.0% |
| 25.0% | 87.4% | 25.0% | 98.5% |

TABLE 1-continued

| Oxidant demand (ppm Chlorine equivalent added) | | | |
|---|---|---|---|
| NaOCl 58 | | NH$_2$Cl 13 | |
| NaOCl (as % of demand) | α-amylase activity | NH$_2$Cl (as % of demand) | α-amylase activity |
| 50/0% | 43.8% | 50.0% | 99.3% |
| 100.0% | 2.1% | 100.0% | 99.1% |

The experimental results show that adding NaOCl at between 10% to 50% of the actual chlorine demand to a high demand solution containing α-amylase was effective to reduce the α-amylase activity. Adding monochloramine to the same samples had no significant effect on the α-amylase activity.

Example 4

This example demonstrates experimental tests used to investigate the presence of starch tightly linked to cellulose fibers in pulp. An experimental test for starch quantification in solution based on chemical oxygen demand (COD) measurement was used. Quantifying starch is typically done using iodine. The problem with this method is that it only works on intact, high molecular weight starch in the correct configuration. Starch molecules in varying degrees of degradation to lower molecular weight starch, sugar oligomers or individual sugars are not detected or measured with iodine. To overcome this problem and have a more robust method to quantify starch and degradation products, chemical oxygen demand (COD) measurements can be used. Especially when starch is known to be the only or main COD contributing molecule in solutions, this method can give very accurate and reproducible numbers that are not affected by the degree to which starch is degraded.

In pulp samples, for example, it was important to be able to determine whether starch was present in pulp samples tightly linked to the cellulose fibers. To determine this, fiber samples were prepared in the lab or industrial fiber samples were analyzed on site. The pulp was recovered for the different suspensions by filtration over a screen, using both 400 micron screens and paper filters as available, and re-suspended in tap water. The pulp was filtered a second time and again re-suspended in tap water. Samples of the pulp prepared like this were subjected to α-amylase activity and after an adequate incubation time again filtered. Also, controls, which were not treated with enzyme, were filtered again. Finally, the COD in these two (2) final (tertiary) filtrates and in the primary filtrate was determined as a measure for the starch bound to the cellulose fibers.

For laboratory samples prepared from cardboard boxes (1% fiber consistency), the following experimental results were obtained:
  unwashed pulp producing the primary filtrate upon filtration, without α-amylase: COD of the primary filtrate>500 ppm. This COD is the organic material released into solution after pulping of cardboard boxes. Much of this COD consists of starch and its various degradation products as well as other organic material not tightly bound to the cellulose fibers;
  tertiary filtrate of fiber resuspended in water not containing any α-amylases, before the last filtration the fiber was left in suspension for 1 hour at 40° C. before filtration: COD of the tertiary filtrate<70 ppm. After 2 washing cycles, almost no more COD is released mechanically from the cellulose fiber material that is retained on the filters;
  tertiary filtrate of fiber resuspended in water, during the last cycle α-amylase was added to the suspension and a contact time of 1 hour at 40° C. was given before filtration: COD of the tertiary filtrate>500 ppm, Adding α-amylase to the last fiber suspension releases a significant amount of organic material from the cellulose fiber that is not removed through simple mechanical means. Based on the specificity of amylase for starch as a substrate it is logical to assume that the COD that was released from the fiber was starch.

In the final test the actual COD measurement was corrected for the COD that was added with the enzyme addition to give the actual COD released from the fiber suspension.

The actual amount of COD released after amylase activity into the tertiary filtrate was similar to the amount of COD release from the primary fiber suspension. Based on this observation it is possible to state that up to 50% or more of the total starch in recycled board pulp can be present in complexes with cellulose fibers that are not disrupted through simple mechanical actions such as repulping.

From these experimental testing results, it is clear that from the total COD/starch present in cardboard box that a significant percentage is tightly linked as starch to the fiber. Protecting it from amylase degradation keeps it tightly associated with fibers, such as by the indicated double treatment method using NaOCl and chloramine, and allows its efficient transfer into a new sheet manufactured with recycled pulp from the cardboard box. On the material tested and the experimental conditions used, this would correspond to almost 50% of the starch in the box to move with the fiber.

Example 5

An industrial trial was conducted at a commercial paper mill to investigate the efficacy of a double treatment method using chloramine and NaOCl on pulp in the production of different grades of paper. During the trial, size press starch usage for a sheet produced from pulp that had been subjected to the indicated double treatment before sheet formation was adjusted such that strength is maintained approximately the same as that obtained for the sheet made from pulp that does not receive the double treatment. To do this, the size press starch usage during the trial was compared to similar product produced outside of the trial period. Also, other variables such as filler evolution (CaCO$_3$) were monitored during the trial. Any increase in filler would normally also be expected to result in a drop in strength characteristics. During the trial, it was seen from the results that starch usage in the size press can be noticeably reduced in the production of different grades of paper while maintaining approximately the same paper strength as sheets produced without the double treatment. Further, a significant increase in filler retention was seen for sheets produced from pulp that had received the double treatment, while at the same time the strength was maintained or slightly increased, and even though the starch usage was reduced in the size press.

The present invention includes the following aspects/embodiments/features in any order and/or in any combination:
1. A method to preserve starch present in pulp comprising:
   in a papermaking process having a head box, treating process water containing said pulp with chloramine comprising monochloramine such that said process water has a residual chloramine amount of from 0.3 ppm to 15 ppm at the head box, wherein starch is present in said pulp in an amount of at least 0.001 wt % based on weight of dried pulp fiber.

2. The method of any preceding or following embodiment/feature/aspect, comprising continuously treating the process water containing said pulp with said chloramine.

3. The method of any preceding or following embodiment/feature/aspect, having a roundformer in place of the headbox.

4. The method of any preceding or following embodiment/feature/aspect, wherein said pulp is from recycled packaging, old corrugated containers (OCC), mixed office waste (MOW), coated fine papers, or any combinations thereof.

5. The method of any preceding or following embodiment/feature/aspect, wherein said pulp is from recycled packaging, old corrugated containers (OCC), mixed office waste (MOW), and/or coated fine paper that contains at least 20 kg/tonne of starch.

6. The method of any preceding or following embodiment/feature/aspect, further comprising forming packaging sheets/boards having a starch content of at least 5 kg/tonne of packaging sheets/boards.

7. The method of any preceding or following embodiment/feature/aspect, wherein production of amylase, such as α-amylase, is controlled or prevented.

8. The method of any preceding or following embodiment/feature/aspect, wherein amylolytic bacteria are present in an amount of less than about $1.0 \times 10^{15}$ cfu/g dry pulp in said process water.

9. The method of any preceding or following embodiment/feature/aspect, wherein amylolytic bacteria are present in an amount of less than about $1.0 \times 10^{10}$ cfu/g pulp d.w. in said process water.

10. The method of any preceding or following embodiment/feature/aspect, wherein amylolytic bacteria are present in an amount of less than about $1.0 \times 10^{5}$ cfu/g pulp d.w. in said process water.

11. The method of any preceding or following embodiment/feature/aspect, wherein said continuously treating comprises at least 12 hours.

12. The method of any preceding or following embodiment/feature/aspect, wherein said continuously treating comprises at least 24 hours.

13. The method of any preceding or following embodiment/feature/aspect, wherein said continuously treating comprises at least 36 hours.

14. The method of any preceding or following embodiment/feature/aspect, wherein said continuously treating comprises at least 7 days.

15. The method of any preceding or following embodiment/feature/aspect, wherein $Ca^{2+}$ ion levels in said process water are less than 1200 ppm.

16. The method of any preceding or following embodiment/feature/aspect, wherein $Ca^{2+}$ ion levels in said process water are less than 1000 ppm.

17. The method of any preceding or following embodiment/feature/aspect, wherein $Ca^{2+}$ ion levels in said process water are less than 800 ppm.

18. The method of any preceding or following embodiment/feature/aspect, wherein said treating occurs at the head box or upstream of said head box.

19. The method of any preceding or following embodiment/feature/aspect, wherein said chloramine is formed as a stock solution that is introduced to said process water.

20. The method of any preceding or following embodiment/feature/aspect, wherein said chloramine is formed in-situ in said process water.

21. The method of any preceding or following embodiment/feature/aspect, wherein said chloramine is formed by reacting at least one ammonium salt with at one chlorine containing oxidant.

22. The method of any preceding or following embodiment/feature/aspect, wherein said chloramine is formed by reacting at least one ammonium salt with sodium hypochlorite or calcium hypochlorite or both.

23. Packaging sheets/boards produced using the method of any preceding or following embodiment/feature/aspect.

24. A method for microorganism control and starch protection in pulp in a papermaking process comprising a dual treatment of process water containing pulp with biocide and oxidant, wherein the biocide reduces microorganisms capable of producing starch-degrading enzymes, and the oxidant reduces enzymatic activity of starch-degrading enzymes on starch content of the pulp.

25. A method to preserve native starch present in pulp comprising:

in a papermaking process, treating process water containing pulp comprising complexes or aggregates of cellulose and native starch, wherein said treating comprises separately adding chloramine and oxidant to said process water, wherein starch-degrading enzyme content in the treated process water is reduced compared to treatment of the process water without the oxidant.

26. The method of any preceding or following embodiment/feature/aspect, wherein the starch-degrading enzyme content is amylase content, such as α-amylase content.

27. The method of any preceding or following embodiment/feature/aspect, wherein the oxidant is sodium hypochlorite.

28. The method of any preceding or following embodiment/feature/aspect, wherein said pulp is from recycled packaging, old corrugated containers (OCC), or broke.

29. The method of any preceding or following embodiment/feature/aspect, wherein production of amylase, such as α-amylase, is prevented.

30. The method of any preceding or following embodiment/feature/aspect, wherein said adding of said sodium hypochlorite or other oxidant comprises adding said sodium hypochlorite or other oxidant at from about 10% to about 50% of actual chlorine demand of said process water.

31. The method of any preceding or following embodiment/feature/aspect, wherein said separately adding said chloramine and said sodium hypochlorite or other oxidant to said process water comprises adding said chloramine to said process water, and after a delay, then adding said sodium hypochlorite or other oxidant to said process water.

32. The method of any preceding or following embodiment/feature/aspect, wherein said adding of said sodium hypochlorite or other oxidant occurs at the pulper or high density chest.

33. Packaging sheets/boards produced using the method of any preceding or following embodiment/feature/aspect.

34. A method to control or prevent calcium precipitation and/or scaling in an aerobic or anaerobic digester that processes process water used in papermaking and that contained calcium from pulp being process, said method comprising in a papermaking process, continuously treating process water containing said pulp with chloramine comprising monochloramine such that said process water when said pulp is present has a residual chloramine amount of from 0.3 ppm to 15 ppm, wherein calcium is present in said pulp, and then forming paper/paperboard from said pulp, and processing said process water, after pulp removal, to one or more digesters.

35. A method to control or prevent calcium precipitation and/or scaling in a biological oxygen demand reduction (BOD) system that processes process water used in papermaking and that contained calcium from pulp being processed, said method comprising in a papermaking process, continuously treating process water containing said pulp with chloramine comprising monochloramine such that said process water when said pulp is present has a residual chloramine amount of from 0.3 ppm to 15 ppm, wherein calcium is present in said pulp, and then forming paper/paperboard from said pulp, and processing said process water, after pulp removal, to said BOD system to reduce BODs.

36. The method of any preceding or following embodiment/feature/aspect, wherein said calcium ion present in the process water after pulp removal is present in an amount of 5000 ppm or less.

37. The method of any preceding or following embodiment/feature/aspect, wherein said calcium ion present in the process water after pulp removal is present in an amount of 2000 ppm or less.

38. The method of any preceding or following embodiment/feature/aspect, wherein said calcium ion present in the process water after pulp removal is present in an amount of 1000 ppm or less.

39. The method of any preceding or following embodiment/feature/aspect, wherein said calcium ion present in the process water after pulp removal is present in an amount of 500 ppm or less.

40. The method of any preceding or following embodiment/feature/aspect, wherein said calcium ion present in the process water after pulp removal is present in an amount of from about 10 ppm to 500 ppm.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method to preserve native starch present in pulp comprising:
in a papermaking process that includes an anaerobic digester, or an aerobic digester, or both, that processes process water, treating process water containing pulp comprising complexes or aggregates of cellulose and native starch, wherein said treating comprises separately adding at different locations chloramine and oxidant to said process water, wherein starch-degrading enzyme content in the treated process water is reduced compared to treatment of the process water without the oxidant, wherein the adding of said oxidant is at sub-demand concentrations such that oxidant is added at from about 10 wt % to about 50 wt % of the actual demand of said process water, wherein actual demand is total amount of chlorine that would be used up in reactions with all chloride-reactable compounds in the process water without leaving residual chlorine therein.

2. The method of claim 1, wherein the starch-degrading enzyme content is amylase content.

3. The method of claim 1, wherein the oxidant is sodium hypochlorite.

4. The method of claim 3, wherein said adding of said sodium hypochlorite comprises adding said sodium hypochlorite at from about 10 wt % to about 50 wt % of actual chlorine demand of said process water.

5. The method of claim 3, wherein said separately adding said chloramine and said sodium hypochlorite to said process water comprises adding said chloramine to said process water, and after a delay, then adding said sodium hypochlorite to said process water.

6. The method of claim 3, wherein said adding of said sodium hypochlorite occurs at a pulper or a high density chest.

7. The method of claim 1, wherein said pulp is from recycled packaging, old corrugated containers (OCC), or broke.

8. The method of claim 1, wherein production of amylase is prevented.

9. The method of claim 1, further comprising forming paper or paperboard or packaging sheets having a starch content that includes the native starch preserved during said method.

10. The method of claim 1, wherein said oxidant is compatible with said monochloramine in that said oxidant does not release free halogen that reacts with said monochloramine.

11. The method of claim 1, wherein said oxidant is incompatible with said monochloramine in that said oxidant releases free halogen that reacts with said monochloramine.

12. The method of claim 1, wherein said oxidant is a hypohalite compound, or a halogenated hydantoin.

13. The method of claim 1, wherein said oxidant is an alkali metal hypohalite or alkaline earth metal hypohalite.

14. The method of claim 1, wherein said adding of said oxidant comprises adding said oxidant at from about 20 wt % to about 40 wt % of the actual demand of said process water.

15. The method of claim 1, wherein said oxidant is added upstream of said chloramine.

* * * * *